US012661184B2

(12) United States Patent
Sun

(10) Patent No.: US 12,661,184 B2
(45) Date of Patent: Jun. 23, 2026

(54) SYSTEMS AND METHODS FOR ASSISTING IN PUNCTURE

(71) Applicant: SHANGHAI UNITED IMAGING HEALTHCARE CO., LTD., Shanghai (CN)

(72) Inventor: Qifei Sun, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 604 days.

(21) Appl. No.: 18/191,857

(22) Filed: Mar. 28, 2023

(65) Prior Publication Data

US 2023/0233260 A1     Jul. 27, 2023

Related U.S. Application Data

(63) Continuation of application No. PCT/CN2020/141691, filed on Dec. 30, 2020.

(30) Foreign Application Priority Data

Sep. 28, 2020    (CN) .......................... 202011043435.6

(51) Int. Cl.
*A61B 34/10*              (2016.01)
(52) U.S. Cl.
CPC ........ *A61B 34/10* (2016.02); *A61B 2034/104* (2016.02); *A61B 2034/105* (2016.02); *A61B 2034/107* (2016.02); *A61B 2034/108* (2016.02)
(58) Field of Classification Search
CPC .............. A61B 34/10; A61B 2034/104; A61B 2034/105; A61B 2034/107;

(Continued)

(56) References Cited

U.S. PATENT DOCUMENTS

| | | | |
|---|---|---|---|
| 2004/0009459 A1* | 1/2004 | Anderson | ............... G06T 19/00 703/11 |
| 2015/0257730 A1 | 9/2015 | Masumoto | |
| 2018/0338795 A1 | 11/2018 | Sugiyama et al. | |

FOREIGN PATENT DOCUMENTS

| | | |
|---|---|---|
| CN | 103892912 A | 7/2014 |
| CN | 104605917 A | 5/2015 |

(Continued)

OTHER PUBLICATIONS

"A navigation system for percutaneous needle interventions based on PET/CT images: Design, workflow and error analysis of soft tissue and bone punctures" by T. Oliveira-Santos et al. Computer Aided Surgery. Sep. 2011. 16(5): 203-219.*

(Continued)

*Primary Examiner* — Jason M Ip

(74) *Attorney, Agent, or Firm* — METIS IP LLC

(57)                ABSTRACT

The present disclosure relates to systems and methods. The method may include obtaining at least one image of an object. The method may include determining a focal point in each of the at least one image. The method may include determining at least one puncture parameter of a puncture operation to be performed on the object based on information associated with the focal point. The method may further include displaying the focal point and a puncture representation of the at least one puncture parameter. The puncture representation may at least indicate a puncture point.

20 Claims, 8 Drawing Sheets

(58) Field of Classification Search
CPC .......... A61B 2034/108; A61B 10/0233; A61B
17/34; A61B 17/3403; G06T 17/00
See application file for complete search history.

(56) References Cited

FOREIGN PATENT DOCUMENTS

| CN | 105310710 A | 2/2016 |
|---|---|---|
| CN | 107392916 A | 11/2017 |
| CN | 107714070 A | 2/2018 |
| CN | 108805933 A | 11/2018 |
| CN | 109394317 A | 3/2019 |
| CN | 109549689 A | 4/2019 |
| CN | 110176300 A | 8/2019 |
| CN | 110192911 A | 9/2019 |
| CN | 110960299 A | 4/2020 |
| WO | 2022062261 A1 | 3/2022 |

OTHER PUBLICATIONS

"Needle Steering and Model-Based Trajectory Planning" by S.P.
DiMaio et al. Medical Image Computing and Computer-Assisted
Intervention MICCAI 2003. pp. 33-40.*
International Search Report in PCT/CN2020/141691 mailed on Jun.
30, 2021, 7 pages.
Written Opinion in PCT/CN2020/141691 mailed on Jun. 30, 2021,
8 pages.
First Office Action in Chinese Application No. 202011043435.6
mailed on Jun. 1, 2021, 16 pages.
Siemens Company, Mammomat Inspiration Tomosynthesis Option,
2015, 78 pages.
Hologic Company, Affirm Breast Biopsy Guidance System Service
Manual, 2019, 116 pages.
General Electric Company, Senographe Essential Stereotaxy Opera-
tor Manual, 2017, 210 pages.

* cited by examiner

300

<u>140</u>

Obtaining Module 410

Focal Point
Determination Module
420

Puncture Parameter
Determination Module
430

Display Module 440

500

510

Obtaining at least one image of an object

520

Determining a focal point in each of the at least one image

530

Determining at least one puncture parameter of a puncture operation to be performed on the object based on information associated with the focal point

540

Displaying the focal point and a puncture representation of the at least one puncture parameter <u>600</u>

Obtaining at least one parameter associated with an object ~⌐ 610

Determining a three-dimensional (3D) model corresponding to the object based on the at least one parameter associated with the object ~⌐ 620

SYSTEMS AND METHODS FOR ASSISTING IN PUNCTURE

CROSS-REFERENCE TO RELATED APPLICATIONS

This application is a continuation of International Application No. PCT/CN2020/141691, filed on Dec. 30, 2020, which claims priority to Chinese Patent Application No. 202011043435.6 filed on Sep. 28, 2020, the contents of each of which are hereby incorporated by reference.

TECHNICAL FIELD

The present disclosure generally relates to image processing, and in particular, to systems and methods for imaging processing associated with puncture.

BACKGROUND

With the development of medical technologies, puncture treatment becomes increasingly common. Since the puncture treatment is an invasive treatment, the accuracy of puncture parameters is very important. Generally, a doctor may manually mark a focal point based on one or more scout images and directly perform the puncture treatment based on the marked focal point. However, after the scout images are obtained and before the puncture treatment is performed, the patient may slightly move voluntarily or involuntarily, which may result in that an actual target point is inconsistent with the predetermined focal point and further affects the accuracy of the puncture treatment. Therefore, it is desirable to provide systems and methods for adjusting the focal point and accordingly adjusting the puncture treatment, thereby improving the puncture accuracy and efficiency.

SUMMARY

According to an aspect of the present disclosure, a method is provided. The method may be implemented on a computing device having at least one processor and at least one storage device. The method may include obtaining at least one image of an object. The method may include determining a focal point in each of the at least one image. The method may include determining at least one puncture parameter of a puncture operation to be performed on the object based on information associated with the focal point. The method may include displaying the focal point and a puncture representation of the at least one puncture parameter. The puncture representation may at least indicate a puncture point.

In some embodiments, the at least one image of the object may include a plurality of images captured by an imaging device from different angles relative to the object.

In some embodiments, the displaying the focal point and the puncture representation of the at least one puncture parameter may include displaying the focal point and the puncture representation of the at least one puncture parameter in the at least one image of the object.

In some embodiments, the displaying the focal point and the puncture representation of the at least one puncture parameter may include displaying the focal point and the puncture representation of the at least one puncture parameter in a three-dimensional (3D) model corresponding to the object.

In some embodiments, the 3D model corresponding to the object is established based on a process. The process may include obtaining at least one parameter associated with the object. The parameter associated with the object may include at least one of a size of the object or a device parameter of a puncture device. The process may include determining the 3D model corresponding to the object based on the at least one parameter associated with the object.

In some embodiments, the at least one puncture parameter may include at least one of a position of the puncture point, a type of a puncture needle, a length of the puncture needle, a diameter of the puncture needle, a puncture direction, a puncture angle, or a puncture depth.

In some embodiments, the method may include simulating a puncture process based on the focal point and the at least one puncture parameter associated with the puncture operation to be performed on the object. The method may further include displaying a simulation result of the simulated puncture process in at least one of the at least one image of the object and/or a 3D model corresponding to the object.

In some embodiments, the method may include determining whether the simulation result satisfies a preset condition. The method may further include adjusting the focal point or the at least one puncture parameter based on the simulation result in response to determining that the simulation result does not satisfy the preset condition.

In some embodiments, the method may include displaying an adjusted focal point or an adjusted puncture representation upon determining that the focal point or at least a portion of the at least one puncture parameter is adjusted. The adjusted puncture representation may at least indicate an adjusted puncture point.

In some embodiments, the method may include updating the puncture representation during the puncture operation in real-time. The method may further include displaying the puncture representation during the puncture in real-time.

According to another aspect of the present disclosure, a system is provided. The system may include at least one storage device including a set of instructions and at least one processor configured to communicate with the at least one storage device. When executing the set of instructions, the at least one processor may be configured to direct the system to perform the following operations. The system may obtain at least one image of an object. The system may determine a focal point in each of the at least one image. The system may determine at least one puncture parameter of a puncture operation to be performed on the object based on information associated with the focal point. The system may display the focal point and a puncture representation of the at least one puncture parameter. The puncture representation may at least indicate a puncture point.

In some embodiments, the system may simulate a puncture process based on the focal point and the at least one puncture parameter associated with the puncture operation to be performed on the object. The system may display a simulation result of the simulated puncture process in at least one of the at least one image of the object and/or a 3D model corresponding to the object.

In some embodiments, the system may further determine whether the simulation result satisfies a preset condition. The system may adjust the focal point or the at least one puncture parameter based on the simulation result in response to determining that the simulation result does not satisfy the preset condition.

In some embodiments, the system may display an adjusted focal point or an adjusted puncture representation upon determining that the focal point or at least a portion of the at least one puncture parameter is adjusted. The adjusted puncture representation may at least indicate an adjusted puncture point.

In some embodiments, the system may update the puncture representation during the puncture operation in real-time. The system may display the puncture representation during the puncture in real-time.

According to yet another aspect of the present disclosure, a non-transitory computer readable medium is provided. The non-transitory computer readable medium may include a set of instructions. When executed by at least one processor, the set of instructions may direct the at least one processor to effectuate a method. The method may include obtaining at least one image of an object. The method may include determining a focal point in each of the at least one image. The method may include determining at least one puncture parameter of a puncture operation to be performed on the object based on information associated with the focal point. The method may include displaying the focal point and a puncture representation of the at least one puncture parameter. The puncture representation may at least indicate a puncture point.

According to yet another aspect of the present disclosure, a system is provided. The system may include an obtaining module, a focal point determination module, a puncture parameter determination module, and a display module. The obtaining module may be configured to obtain at least one image of an object. The focal point determination module may be configured to determine a focal point in each of the at least one image. The puncture parameter determination module may be configured to determine at least one puncture parameter of a puncture operation to be performed on the object based on information associated with the focal point. The display module may be configured to display the focal point and a puncture representation of the at least one puncture parameter. The puncture representation may at least indicate a puncture point.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

Figure 1:
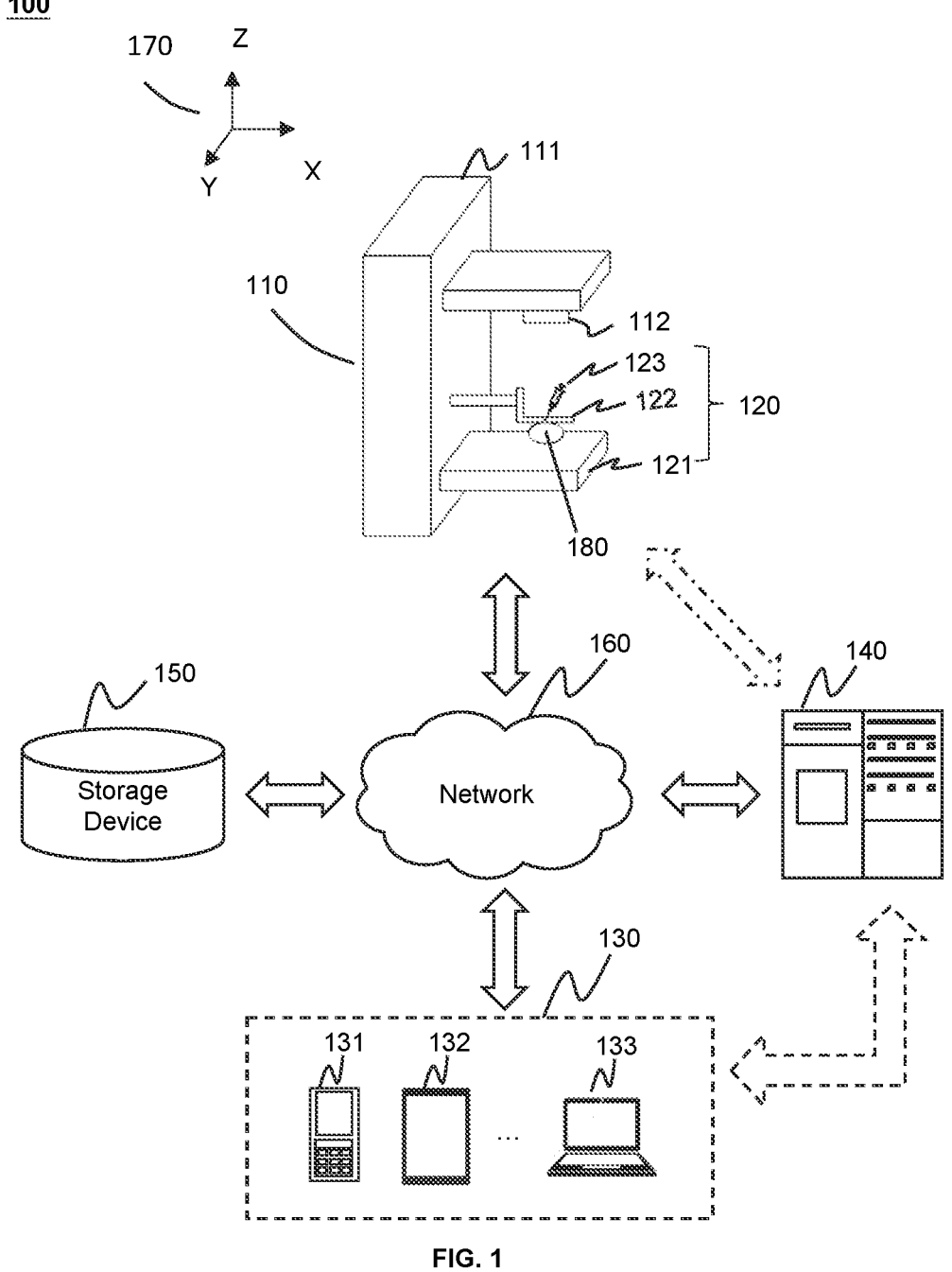
FIG. 1 is a schematic diagram illustrating an exemplary medical system according to some embodiments of the present disclosure.

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the terms "system," "engine," "unit," "module," and/or "block" used herein are one method to distinguish different components, elements, parts, sections, or assemblies of different level in ascending order. However, the terms may be displaced by another expression if they achieve the same purpose.

Generally, the words "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., a processor 210 illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included in programmable units, such as programmable gate arrays or processors. The modules/units/blocks or computing device functionality described herein may be implemented as software modules/units/blocks but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module, or block is referred to as being "on," "connected to," or "coupled to," another unit, engine, module, or block, it may be directly on, connected or coupled to, or communicate with the other unit, engine, module, or block, or an intervening unit, engine, module, or block may be present unless the context clearly indicates otherwise. As used herein, the term "and/or" includes any and all combinations of one or more of the associated listed items. The term "image" in the present disclosure is used to collectively refer to image data (e.g., scan data, projection data) and/or images of various forms, including a two-dimensional (2D) image, a three-dimensional (3D) image, a four-dimensional (4D), etc. The term "pixel" and "voxel" in the present disclosure are used interchangeably to refer to an element of an image.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

Provided herein are systems and methods for non-invasive biomedical imaging, such as for disease diagnostic or research purposes. In some embodiments, the systems may include a single modality imaging system and/or a multi-modality imaging system. The single modality imaging system may include, for example, an ultrasound imaging system, an X-ray imaging system, an computed tomography (CT) system, a magnetic resonance imaging (MRI) system, an ultrasonography system, a positron emission tomography (PET) system, an optical coherence tomography (OCT) imaging system, an ultrasound (US) imaging system, an intravascular ultrasound (IVUS) imaging system, a near infrared spectroscopy (N IRS) imaging system, or the like, or any combination thereof. The multi-modality imaging system may include, for example, an X-ray imaging-magnetic resonance imaging (X-ray-MRI) system, a positron emission tomography-X-ray imaging (PET-X-ray) system, a single photon emission computed tomography-magnetic resonance imaging (SPECT-MRI) system, a positron emission tomography-computed tomography (PET-CT) system, a C-arm system, a digital subtraction angiography-magnetic resonance imaging (DSA-MRI) system, etc. It should be noted that the imaging system described below is merely provided for illustration purposes, and not intended to limit the scope of the present disclosure.

The term "imaging modality" or "modality" as used herein broadly refers to an imaging method or technology that gathers, generates, processes, and/or analyzes imaging information of an object. The object may include a biological object and/or a non-biological object. The biological object may be a human being, an animal, a plant, or a portion thereof (e.g., a cell, a tissue, an organ). In some embodiments, the object may be a man-made composition of organic and/or inorganic matters that are with or without life.

In the present disclosure, the term "puncture" and the term "puncture operation" can be used interchangeably.

An aspect of the present disclosure relates to systems and methods for assisting in a puncture operation. The systems may obtain at least one image of an object and determine a focal point in each of the at least one image. The systems may determine at least one puncture parameter of a puncture operation to be performed on the object based on information associated with the focal point. The systems may display the focal point and a puncture representation of the at least one puncture parameter to provide a reference for a doctor or an operator. Specifically, the systems may display the focal point and the puncture representation of the at least one puncture parameter in the at least one image (or newly captured image(s)) of the object and/or a 3D model corresponding to the object.

According to the embodiments of the present disclosure, the display of the focal point and the puncture representation of the at least one puncture parameter can provide a reference for a doctor or an operator. Further, according to the focal point and the puncture representation of the at least one puncture parameter, the doctor or the operator can accurately perform the puncture operation on the object or adjust the focal point and/or the at least one puncture parameters, during which the display of the focal point and the puncture representation of the at least one puncture parameter also may be updated in real-time. Accordingly, the accuracy and efficiency of the puncture can be significantly improved.

FIG. 1 is a schematic diagram illustrating an exemplary medical system according to some embodiments of the present disclosure. As illustrated in FIG. 1, the medical system 100 may include an imaging device 110, a puncture device 120, a terminal device 130, a processing device 140, a storage device 150, and a network 160. The components in the medical system 100 may be connected in one or more of various ways. For example, the imaging device 110 and/or the puncture device 120 may be connected to the processing device 140 through the network 160. As another example, the imaging device 110 may be connected to the processing device 140 directly as indicated by the bi-directional arrow in dotted lines linking the imaging device 110 and the processing device 140. As a further example, the storage device 150 may be connected to the processing device 140 directly or through the network 160. As still a further example, the terminal device 130 may be connected to the processing device 140 directly (as indicated by the bi-directional arrow in dotted lines linking the terminal device 130 and the processing device 140) or through the network 160.

The imaging device 110 may generate or provide image data related to an object 180 via scanning the object 180. In some embodiments, the object 180 may include a biological object and/or a non-biological object. For example, the object 180 may include a specific portion of a body, such as a head, a thorax, an abdomen, a breast, or the like, or a combination thereof. In some embodiments, the imaging device 110 may include a single-modality scanner (e.g., a CT scanner) and/or a multi-modality scanner (e.g., a PET-CT scanner) as described elsewhere in this disclosure. In some embodiments, the image data relating to the object 180 may include one or more scout images, one or more reconstruction images, projection data, etc. As used herein, the projection data may include raw data generated by the imaging device 110 by scanning the object 180 and/or data generated by performing a projection on the raw data or an image of the object 180.

The puncture device 120 may be configured to perform a puncture operation on the object 180 automatically or semi-automatically based on image data obtained by the imaging device 110. As used herein, "automatically" may refer to that the puncture device 120 performs the puncture operation automatically; "semi-automatically" may refer to that the puncture device 120 performs the puncture operation with user intervention. The user intervention may include, for example, providing information (e.g., a location of a lesion) regarding the object 180, providing information (e.g., at least one puncture parameter) regarding the puncture operation, or the like, or a combination thereof.

In some embodiments, the imaging device 110 may include a gantry 111, a radioactive scanning source 112, and a detector (not shown). The puncture device 120 may include a scanning table 121, a compression panel 122, and a puncture unit 123.

The gantry 111 may be configured to support the radioactive scanning source 112, the scanning table 121, and the compression panel 122.

The radioactive scanning source 112 may emit radioactive rays to the object 180 placed on the scanning table 121. The radiation may include a particle ray, a photon ray, or the like, or a combination thereof. In some embodiments, the radiation may include a plurality of radiation particles (e.g., neutrons, protons, electrons, p-mesons, heavy ions), a plurality of radiation photons (e.g., X-ray, a y-ray, ultraviolet, laser), or the like, or a combination thereof.

The detector may be disposed in the scanning table 121 and may detect radiations and/or radiation events (e.g., gamma photons) passed through the object 180. In some embodiments, the detector may include a plurality of detector units. The detector unit may include a scintillation detector (e.g., a cesium iodide detector) or a gas detector. The detector unit may be a single-row detector or a multi-rows detector.

The scanning table 121 may be configured to support the object 180 and/or one or more other components (e.g., a detector) of the imaging device 110 and/or the puncture device 120.

The compression panel 122 may be configured to compress the object 180 placed on the scanning table 121. In some embodiments, the compression panel 122 may include an opening via which one or more operations may be performed on the object 180. For example, the puncture device 120 may perform a puncture operation on the object 180 through the opening of the compression panel 122. In some embodiments, a shape of the opening may include a square, a rectangle, a triangle, a polygon, a circle, an ellipse, an irregular shape, etc.

The puncture unit 123 may be configured to perform the puncture operation on the object 180. In some embodiments, the puncture unit 123 may include a biopsy needle, a puncture needle, an ablation needle, an ablation probe, a drill bit, a hook wire, or the like, or any combination thereof.

In some embodiments, the puncture device 120 may further include one or more other components, such as a firing actuator, a guiding device, a location detection device, a positioning mechanism, a mounting mechanism, etc.

The terminal device 130 may include a mobile device 131, a tablet computer 132, a laptop computer 133, or the like, or any combination thereof. In some embodiments, the mobile device 131 may include a smart home device, a wearable device, a smart mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, footgear, eyeglasses, a helmet, a watch, clothing, a backpack, an accessory, or the like, or any combination thereof. In some embodiments, the smart mobile device may include a smartphone, a personal digital assistant (PDA), a gaming device, a navigation device, a point of sale (POS) device, or the like, or any combination thereof. In some embodiments, the virtual reality device and/or the augmented reality device may include a virtual reality helmet, a virtual reality glass, a virtual reality patch, an augmented reality helmet, an augmented reality glass, an augmented reality patch, or the like, or any combination thereof. For example, the virtual reality device and/or the augmented reality device may include a Google Glass™ an Oculus Rift™, a HoloLens™, a Gear VR™, etc.

In some embodiments, the terminal device 130 may remotely operate the imaging device 110. In some embodiments, the terminal device 130 may operate the imaging device 110 via a wireless connection. In some embodiments, the terminal device 130 may receive information and/or instructions inputted by a user, and send the received information and/or instructions to the imaging device 110 or the processing device 140 via the network 160. In some embodiments, the terminal device 130 may receive data and/or information from the processing device 140. In some embodiments, the terminal device 130 may be omitted or be part of the processing device 140.

The processing device 140 may process data obtained from the imaging device 110, the terminal device 130, and/or the storage device 150. For example, the processing device 140 may obtain at least one image of the object 180 and determine a point (e.g., a focal point, a puncture point) in the at least one image of the object 180. In some embodiments, the processing device 140 may include a central processing unit (CPU), a digital signal processor (DSP), a system on a chip (SoC), a microcontroller unit (MCU), or the like, or any combination thereof. In some embodiments, the processing device 140 may be local or remote. For example, the processing device 140 may access information and/or data stored in the imaging device 110, the terminal device 130, and/or the storage device 150 via the network 160. As another example, the processing device 140 may be directly connected to the imaging device 110, the terminal device 130, and/or the storage device 150, to access stored information and/or data. In some embodiments, the processing device 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing device 140 may be implemented on a computing device 200 having one or more components illustrated in FIG. 2 in the present disclosure.

The storage device 150 may store data and/or instructions. In some embodiments, the storage device 150 may store data obtained from the imaging device 110, the terminal device 130, and/or the processing device 140. For example, the storage device 150 may store at least one image of the object 180 obtained from the processing device 140 and/or the imaging device 110. As another example, the storage device 150 may store a device parameter of the imaging device 110 and/or the puncture device 120. As yet another example, the storage device 150 may store at least one parameter (e.g., a size, a shape) associated with the object 180. In some embodiments, the storage device 150 may store data and/or instructions that the processing device 140 may execute or use to perform exemplary methods described in the present disclosure. For example, the storage device 150 may store data and/or instructions that the processing device 140 may execute or use to generate a 3D model corresponding to the object 180. In some embodiments, the storage device 150 may include a mass storage device, a removable storage device, a volatile read-and-write memory, a read-only memory (ROM), or the like, or any combination thereof. Exemplary mass storage devices may include a magnetic disk, an optical disk, a solid-state drive, etc. Exemplary removable storage devices may include a flash drive, a floppy disk, an optical disk, a memory card, a zip disk, a magnetic tape, etc. Exemplary volatile read-and-write memory may include a random-access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 150 may be connected to the network 160 to communicate with one or more components (e.g., the imaging device 110, the terminal device 130, the processing device 140) of the medical system 100. One or more components of the medical system 100 may access the data or instructions stored in the storage device 150 via the network 160. In some embodiments, the storage device 150 may be directly connected to or communicate with one or more components (e.g., the imaging device 110, the terminal device 130, the processing device 140) of the medical system 100. In some embodiments, the storage device 150 may be part of the processing device 140.

The network 160 may facilitate the exchange of information and/or data. In some embodiments, one or more components (e.g., the imaging device 110, the terminal device 130, the processing device 140, or the storage device 150) of the medical system 100 may send information and/or data to another component(s) of the medical system 100 via the network 160. For example, the processing device 140 may obtain, via the network 160, at least one image (e.g., scout images) from the storage device 150. As another example, the processing device 140 may obtain a 3D model corresponding to the object 180 from the storage device 150. In some embodiments, the network 160 may be any type of wired or wireless network, or combination thereof. The network 160 may be and/or include a public network (e.g., the Internet), a private network (e.g., a local area network (LAN), a wide area network (WAN))), a wired network (e.g., an Ethernet network), a wireless network (e.g., an 802.11 network, a Wi-Fi network), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 160 may include a cable network, a wireline network, an optical fiber network, a telecommunications network, an intranet, an Internet, a local area network (LAN), a wide area network (WAN), a wireless local area network (WLAN), a metropolitan area network (MAN), a wide area network (WAN), a public telephone switched network (PSTN), a Bluetooth™ network, a ZigBee™ network, a near field communication (NFC) network, or the like, or any combination thereof. In some embodiments, the network 160 may include one or more network access points. For example, the network 160 may include wired or wireless network access points such as base stations and/or internet exchange points through which one or more components of the medical system 100 may be connected to the network 160 to exchange data and/or information.

In some embodiments, a coordinate system may be provided for the medical system 100 to define a position of a component and/or the object 180 (e.g., an absolute position or a position relative to another component). For illustration purposes, the coordinate system 170 may include an X-axis, a Y-axis, and a Z-axis. The X-axis and the Y-axis shown in FIG. 1 may be horizontal, and the Z-axis may be vertical. As illustrated, a positive X direction along the X-axis may be from the inside of the imaging device 110 to the outside of the imaging device 110 viewed from the direction facing the front of the imaging device 110, a positive Y direction along the Y-axis may be from the left side to the right side of the scanning table 121 viewed from the direction facing the front of the imaging device 110, and a positive Z direction along the Z-axis may be from the lower part (or from the floor where the medical system 100 stands) to the upper part of the gantry 111.

It should be noted that the above description of the medical system 100 is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments.

In some embodiments, the medical system 100 may include one or more additional components. For example, the imaging device 110 may include a robotic arm configured to insert the puncture unit 123 into the object 180 to perform the puncture operation on the object 180. Additionally or alternatively, one or more components of the medical system 100 described above may be omitted or two or more components of the medical system 100 may be integrated into a single component. For example, the terminal device 130 and the imaging device 110 may be integrated into a signal component, and the operator may interface with the imaging device 110 through the terminal device 130. As another example, the imaging device 110 and the puncture device 120 may be combined as a single device (e.g., a mammary puncture device) to perform functions of the imaging device 110 and the puncture device 120.

In some embodiments, the imaging device 110 may include a movement control mechanism and a position-limiting mechanism. The movement control mechanism may be assembled on the scanning table 121 and configured to control a movement of the puncture device 120. The position-limiting mechanism may be movably mounted on the scanning table 121 and configured to limit a position of the movement control mechanism during a movement of the movement control mechanism.

Figure 2:
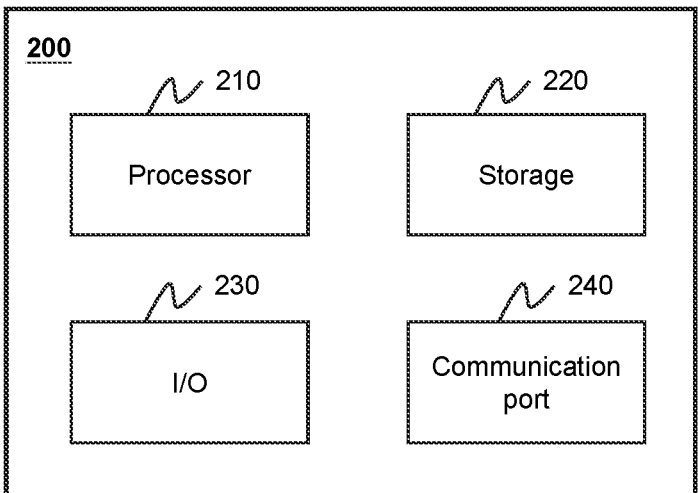
FIG. 2 is a schematic diagram illustrating exemplary hardware and/or software components of an exemplary computing device according to some embodiments of the present disclosure.

FIG. 2 is a schematic diagram illustrating exemplary hardware and/or software components of an exemplary computing device according to some embodiments of the present disclosure. The computing device 200 may be used to implement any component of the medical system 100 as described herein. For example, the processing device 140 and/or the terminal device 130 may be implemented on the computing device 200, respectively, via its hardware, software program, firmware, or a combination thereof. Although only one such computing device is shown, for convenience, the computer functions relating to the medical system 100 as described herein may be implemented in a distributed fashion on a number of similar platforms, to distribute the processing load.

As illustrated in FIG. 2, the computing device 200 may include a processor 210, a storage 220, an input/output (I/O) 230, and a communication port 240.

The processor 210 may execute computer instructions (program code) and, when executing the instructions, cause the processing device 140 to perform functions of the processing device 140 in accordance with techniques described herein. The computer instructions may include, for example, routines, programs, objects, components, signals, data structures, procedures, modules, and functions, which perform particular functions described herein. In some embodiments, the processor 210 may process data and/or images obtained from the imaging device 110, the terminal device 130, the storage device 150, and/or any other component of the medical system 100. For example, the processor 210 may obtain at least one image of the object 180 from the storage device 150.

In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors. Thus operations and/or method steps that are performed by one processor as described in the present disclosure may also be jointly or separately performed by the multiple processors. For example, if in the present disclosure the processor of the computing device 200 executes both operation A and operation B, it should be understood that operation A and operation B may also be performed by two or more different processors jointly or separately in the computing device 200 (e.g., a first processor executes process A and a second processor executes process B, or the first and second processors jointly execute operations A and B).

The storage 220 may store data/information obtained from the imaging device 110, the terminal device 130, the storage device 150, or any other component of the medical system 100. In some embodiments, the storage 220 may include a mass storage device, a removable storage device, a volatile read-and-write memory, a read-only memory (ROM), or the like, or any combination thereof. In some embodiments, the storage 220 may store one or more programs and/or instructions to perform exemplary methods described in the present disclosure.

The I/O 230 may input or output signals, data, and/or information. In some embodiments, the I/O 230 may enable user interaction with the processing device 140. In some embodiments, the I/O 230 may include an input device and an output device. Exemplary input devices may include a keyboard, a mouse, a touch screen, a microphone, or the like, or a combination thereof. Exemplary output devices may include a display device, a loudspeaker, a printer, a projector, or the like, or a combination thereof. Exemplary display devices may include a liquid crystal display (LCD), a light-emitting diode (LED)-based display, a flat panel display, a curved screen, a television device, a cathode ray tube (CRT), or the like, or a combination thereof.

The communication port 240 may be connected to a network (e.g., the network 160) to facilitate data communications. The communication port 240 may establish connections between the processing device 140 and the imaging device 110, the terminal device 130, or the storage device 150. The connection may be a wired connection, a wireless connection, or a combination of both that enables data transmission and reception. The wired connection may include an electrical cable, an optical cable, a telephone wire, or the like, or any combination thereof. The wireless connection may include Bluetooth, Wi-Fi, WiMAX, WLAN, ZIGBEE, mobile network (e.g., 3G, 4G, or 5G), or the like, or a combination thereof. In some embodiments, the communication port 240 may be a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3:
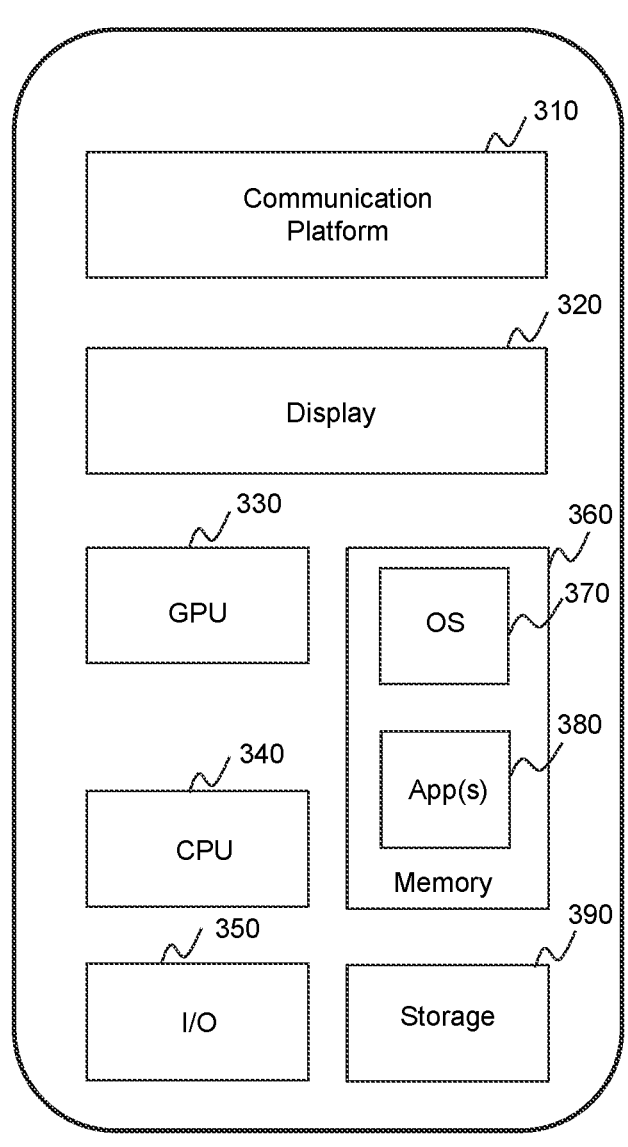
FIG. 3 is a schematic diagram illustrating exemplary hardware and/or software components of an exemplary mobile device according to some embodiments of the present disclosure.

FIG. 3 is a schematic diagram illustrating exemplary hardware and/or software components of an exemplary mobile device according to some embodiments of the present disclosure. In some embodiments, the processing device 140 and/or the terminal device 130 may be implemented on the mobile device 300.

As illustrated in FIG. 3, the mobile device 300 may include a communication platform 310, a display 320, a graphics processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS, Android, or Windows Phone) and one or more applications 380 may be loaded into the memory 360 from the storage 390 in order to be executed by the CPU 340. The applications 380 may include a browser or any other suitable mobile apps for receiving and rendering information relating to the medical system 100. User interactions with the information stream may be achieved via the I/O 350 and provided to the processing device 140 and/or other components of the medical system 100 via the network 160.

To implement various modules, units, and their functionalities described in the present disclosure, computer hardware platforms may be used as the hardware platform(s) for one or more of the elements described herein. The hardware elements, operating systems, and programming languages of such computers are conventional in nature, and it is presumed that those skilled in the art are adequately familiar therewith to adapt those technologies to generate a high-quality image of an object as described herein. A computer with user interface elements may be used to implement a personal computer (PC) or another type of work station or terminal device, although a computer may also act as a server if appropriately programmed. It is believed that those skilled in the art are familiar with the structure, programming, and general operation of such computer equipment and as a result, the drawings should be self-explanatory.

Figure 4:
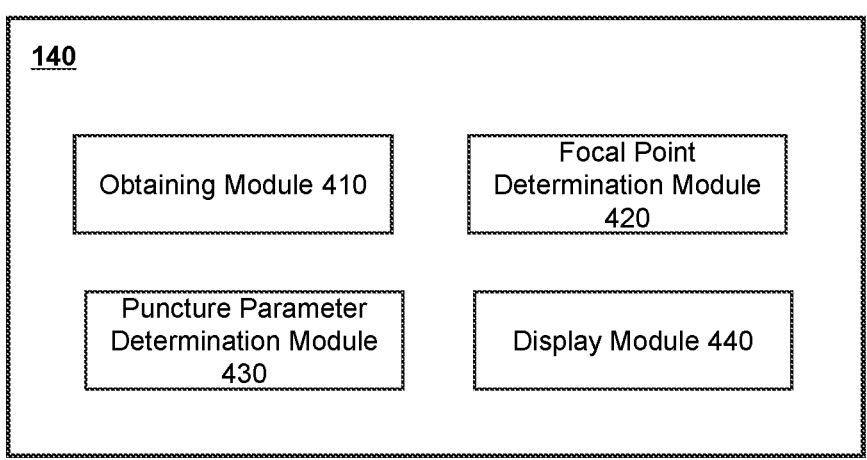
FIG. 4 is block diagrams illustrating an exemplary processing device according to some embodiments of the present disclosure.

FIG. 4 is a block diagram illustrating an exemplary processing device according to some embodiments of the present disclosure. The processing device 140 may include an obtaining module 410, a focal point determination module 420, a puncture parameter determination module 430, and a display module 440.

The obtaining module 410 may be configured to obtain at least one image of an object. Each of the at least one image may include a region of interest (ROI). In some embodiments, the at least one image of the object may be captured by an imaging device (e.g., the imaging device 110) e.g., from different angles relative to the object. In some embodiments, the at least one image of the object may include a scout image of the object, at least one projection image of the object, etc. In some embodiments, the obtaining module 410 may obtain at least one parameter associated with the object. The at least one parameter associated with the object may include a size (e.g., a length, a width, a thickness) of the object, a shape of the object, a device parameter of a puncture device (e.g., the puncture device 120), a device parameter of an imaging device (e.g., the imaging device 110), or the like, or a combination thereof. In some embodiments, the obtaining module 410 may obtain the at least one image and/or the at least one parameter associated with the object from one or more components (e.g., the imaging device 110, the storage device 150, the storage 220, or the storage 390) of the medical system 100 or an external storage device.

The focal point determination module 420 may be configured to determine a focal point in each of the at least one image. In some embodiments, the focal point in each of the at least one image may be determined manually, semi-automatically, or automatically. More descriptions regarding the determination of the focal point may be found elsewhere in the present disclosure (e.g., operation 520 as described in connection with FIG. 5 and the relevant descriptions thereof.).

The puncture parameter determination module 430 may be configured to determine at least one puncture parameter of a puncture operation to be performed on the object based on information associated with the focal point. In some embodiments, the puncture parameter may include a position of a puncture point, a type of a puncture needle, a length of the puncture needle, a diameter of the puncture needle, a puncture direction, a puncture angle, a puncture depth, or the like, or any combination thereof. In some embodiments, the puncture parameter determination module 430 may determine the at least one puncture parameter manually, semi-automatically, or automatically. More descriptions regarding the determination of the at least one puncture parameter may be found elsewhere in the present disclosure (e.g., operation 530 as described in connection with FIG. 5 and the relevant descriptions thereof.).

The display module 440 may be configured to display the focal point and a puncture representation of the at least one puncture parameter. In some embodiments, the display module 440 may display the focal point and the puncture representation of the at least one puncture parameter in the at least one image of the object. In some embodiments, the display module 440 may display the focal point and the puncture representation of the at least one puncture parameter in a 3D model corresponding to the object. In some embodiments, the 3D model corresponding to the object may be determined based on at least one parameter associated with the object. The parameter associated with the object may include at least one of a size of the object or a device parameter of a puncture device.

The modules in the processing device 140 may be connected to or communicate with each other via a wired connection or a wireless connection. The wired connection may include a metal cable, an optical cable, a hybrid cable, or the like, or any combination thereof. The wireless connection may include a Local Area Network (LAN), a Wide Area Network (WAN), a Bluetooth, a ZigBee, a Near Field Communication (NFC), or the like, or any combination thereof. Two or more of the modules may be combined as a single module, and any one of the modules may be divided into two or more units. For example, the focal point determination module 420 and the puncture parameter determination module 430 may be combined as an output module which may be configured to perform the functions thereof. As another example, the processing device 140 may further include a communication module configured to perform corresponding functions to a user instruction.

Figure 5:
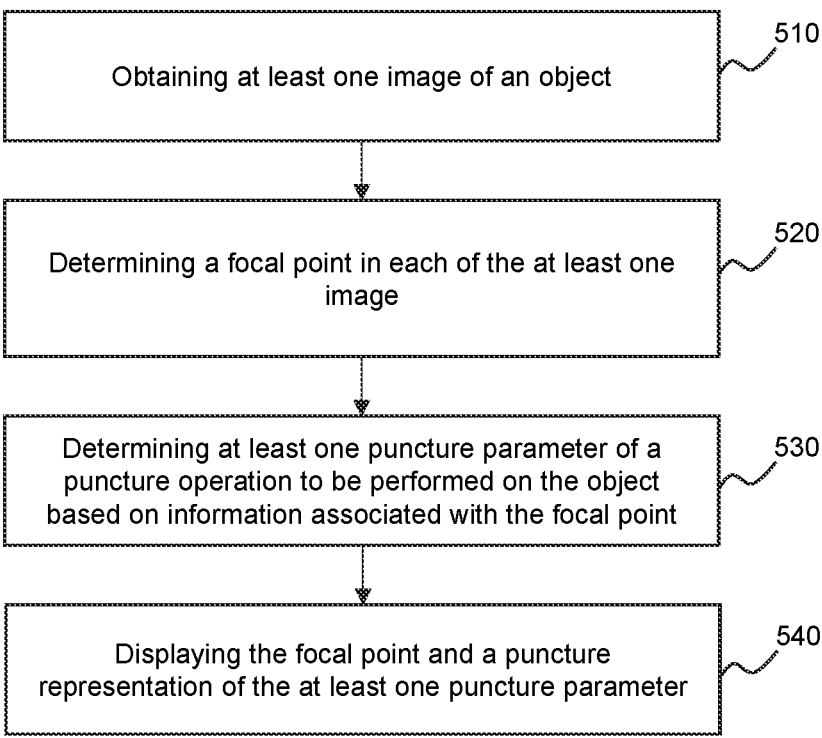
FIG. 5 is a flowchart illustrating an exemplary process for determining a focal point and at least one puncture parameter according to some embodiments of the present disclosure.

FIG. 5 is a flowchart illustrating an exemplary process for determining a focal point and at least one puncture parameter according to some embodiments of the present disclosure. In some embodiments, one or more operations of process 500 illustrated in FIG. 5 may be implemented in the medical system 100 illustrated in FIG. 1. For example, the process 500 may be stored in a storage device (e.g., the storage device 150, the storage 220, and/or the storage 390) of the medical system 100 in the form of instructions, and invoked and/or executed by the processing device 140 (e.g., the processor 210, the CPU 340, or one or more modules illustrated in FIG. 4). The operations of the illustrated process presented below are intended to be illustrative. In some embodiments, the process 500 may be accomplished with one or more additional operations not described and/or without one or more of the operations discussed. Additionally, the order in which the operations of the process as illustrated in FIG. 5 and described below is not intended to be limiting.

In 510, the processing device 140 (e.g., the obtaining module 410) may obtain at least one image of an object (e.g., the object 180).

In some embodiments, the object may include a biological object and/or a non-biological object. For example, the object may include a body of a patient or a specific portion of the body, such as the abdomen, the head, the thorax, the breast, or the like, or a combination thereof.

In some embodiments, each of the at least one image may include an ROI.

For example, it is assumed that the image is an image of the body of the patient, the ROI of the image may represent a specific organ, a specific tissue, or the whole body of the patient. As another example, it is assumed that the image is an image of a specific portion of the body, the ROI of the image may represent a lesion region of the specific portion of the patient. Merely by way of example, the image may be an image of the breast of the patient and the ROI of the image may represent a cancer region, a lump region, a hydrops region, a node region, etc.

In some embodiments, the at least one image may include but not limited to a CT image, an MRI image, an X-ray image, a PET image, an OCT image, a US image, an IVUS image, a NIRS image, or the like, or a combination thereof. In some embodiments, the at least one image may be captured by an imaging device (e.g., the imaging device 110). For example, the at least one image of the object may include a plurality of images captured by the imaging device from different angles relative to the object. As used herein, the angle of the imaging device relative to the object may be equal to a rotation angle (e.g., $\alpha_1$ and $\alpha_2$ illustrated in FIG. 7) of a radioactive scanning source (e.g., the radioactive scanning source 112), which may be an angle between a line connecting the radioactive scanning source and a detector and a vertical direction (e.g., the Z-axis direction of the coordinate system 170). In some embodiments, the rotation angle of the radioactive scanning source may be determined manually by a user (e.g., a doctor or a maintenance person), automatically by the processing device 140, or semi-automatically by the user and the processing device 140. In some embodiments, it is assumed that the vertical direction is denoted as 0°, a negative angle indicates an anti-clockwise rotation of the radioactive scanning source, and a positive angle indicates a clockwise rotation of the radioactive scanning source, the rotation angle of the radioactive scanning source may be within a predetermined range (e.g., [−45°, +45°], [−30°, +30°], [−20°, +20°], [−18°, +18°], [−15°, +15°], [−10°, +10°], [−5°, +5°]).

In some embodiments, the at least one image of the object may include a scout image of the object. As used herein, a scout image may refer to an image indicating position information associated with the object and may be used to assist in the planning of a scan performed on the object by an imaging device (e.g., the imaging device 110). In some embodiments, the scout image may be obtained by a pre-scanning. The pre-scanning may be a CT scanning, an MR scanning, a PET scanning, or the like, or a combination thereof. For example, when a surgery needs to be performed or has been performed on the head of the object to remove a tumor in the head, a pre-scanning may be performed on the object to obtain a scout image of the head indicating position information associated with the tumor. Then the surgery may be performed on the head based on the scout image.

In some embodiments, the at least one image of the object may include at least one projection image of the object. As used herein, the projection image refers to a two-dimensional (2D) projection image obtained by projecting a three-dimensional (3D) image along a predetermined projection direction (or to a predetermined projection plane). In some embodiments, the predetermined direction may be parallel to or vertical to a puncture direction along which a puncture operation may be performed on the object. Accordingly, the projection plane may be parallel to or vertical to the puncture direction. For example, it is assumed that the puncture direction is along the Z-axis of the coordinate system 170, the projection plane may be the XOZ plane or the YOZ plane.

In some embodiments, the processing device 140 may obtain the at least one image from one or more components of the medical system 100. For example, the processing device 140 may obtain the at least one image from the imaging device 110. As another example, the processing device 140 may obtain the at least one image from a storage device (e.g., the storage device 150, the storage 220, or the storage 390) of the medical system 100 via a network (e.g., the network 160). Alternatively or additionally, the processing device 140 may obtain the at least one image from an external source (e.g., a medical database) via a network (e.g., the network 160).

In 520, the processing device 140 (e.g., the focal point determination module 420) may determine a focal point in each of the at least one image.

In some embodiments, the focal point may be a point (e.g., focal point $P_1$ or focal point $P_2$ illustrated in FIG. 7) representing a physical point (e.g., $P_0$ illustrated in FIG. 7) of the object. For example, the focal point may be a feature point (e.g., a shoulder joint, a knee joint, an elbow joint, an ankle joint, a lesion point) of the object in the image. As another example, the focal point may be a point (e.g., a gravity point, a center point, an edge point) in an ROI of the image. Merely by way of example, the ROI of a specific image may represent a lesion region of a specific portion of the object, and the focal point may be a point representing a point (e.g., an edge point, a physical point with a relatively high density, a center point, a gravity point) of the lesion region.

In some embodiments, the focal point in each of the at least one image may be determined manually, semi-automatically, or automatically. For example, each of the at least one image of the object may be transmitted to a terminal device (e.g., the terminal device 130) and a user (e.g., a doctor or an operator) may mark the focal point in the image via a user interface implemented on the terminal device. As another example, the processing device 140 may identify the focal point in each of the at least one image automatically without user intervention. The automatic determination of the focal point may be performed according to an image analysis technique (e.g., an image segmentation algorithm, an object recognition algorithm), a machine learning-based technique (e.g., a trained neural network model for feature point detection), or the like, or any combination thereof. As yet another example, the focal point may be determined semi-automatically by the processing device 140 with user intervention. In some embodiments, the user intervention may include a parameter relating to the image analysis technique, a position parameter relating to the focal point, an adjustment or a confirmation relating to a preliminary focal point determined by the processing device 140, etc.

In 530, the processing device 140 (e.g., the puncture parameter determination module 430) may determine at least one puncture parameter of a puncture operation to be performed on the object based on information associated with the focal point.

In some embodiments, the puncture parameter may include a position of a puncture point, a type of a puncture needle, a length of the puncture needle, a diameter of the puncture needle, a puncture direction, a puncture angle, a puncture depth, or the like, or any combination thereof. As used herein, the puncture point refers to a point (e.g., a real-time tip point of the puncture needle, a start point on a body surface of the object at which the puncture needle may be inserted into the object) on or near a body surface of the object where a puncture needle is located (or where the puncture needle is estimated to be located). The puncture direction refers to a direction along which the puncture needle may be inserted into the object. The puncture angle refers to an angle between the puncture direction and a reference direction (e.g., a direction parallel to or vertical to the body surface of the object). The puncture depth refers to a distance between the puncture point and the focal point in the object, that is, an insertion length of the puncture needle.

In some embodiments, the processing device 140 may automatically determine the at least one puncture parameter based on information (e.g., position information of the focal point, object information (e.g., a size of the object, a shape of the object, a compressed (e.g., compressed by the compression panel 122) thickness of the object), environmental information) associated with the focal point. For example, it is assumed that the focal point is close to the body surface of the object, the processing device 140 may select a puncture needle with a relatively small diameter and determine the puncture direction as a horizontal or a substantially horizontal direction (e.g., the Y-axis or X-axis direction in the coordinate system 170). As another example, it is assumed that the focal point is relatively far from the body surface of the object, the processing device 140 may select a puncture needle with a relatively long length and determine the puncture direction as a vertical or a substantially vertical direction (e.g., the negative Z-axis direction in the coordinate system 170).

In some embodiments, the at least one puncture parameter may be determined manually by a user (e.g., a doctor or an operator) via the terminal device 130 or semi-automatically by the user and the processing device 140. For example, according to position information of the focal point, the user may manually mark the puncture point in the at least one image via the terminal device 130. As another example, the processing device 140 may determine one or more candidate puncture parameters. The candidate puncture parameter(s) may include one or more candidate puncture points, one or more candidate puncture needles, one or more candidate puncture directions, one or more candidate puncture depths, etc. The user may select target puncture parameter(s) from the candidate puncture parameter(s).

In 540, the processing device 140 (e.g., the display module 440) may display the focal point and a puncture representation of the at least one puncture parameter.

As used herein, the puncture representation refers to an expression (e.g., a mathematical expression, a graphical expression (e.g., a graphical model)) that describes the at least one puncture parameter. For example, the puncture representation may be an expression at least indicating the puncture point. Merely by way of example, the puncture representation may include a point, a line, a region, a figure, a text, a simulated object, or the like, or any combination thereof.

In some embodiments, the processing device 140 may display the focal point and the puncture representation of the at least one puncture parameter in various forms, for example, a graphical illustration, a text description, a voice description, an audio description, etc. In some embodiments, the processing device 140 may display various information in different forms (e.g., different colors, different types). For example, the processing device 140 may display the focal point via a filled dot and display the puncture point via a hollow dot. As another example, the processing device 140 may display the focal point and the puncture point via black dots and display a distance between them in red color.

In some embodiments, the focal point and the puncture representation of the at least one puncture parameter may be displayed automatically, semi-automatically, or manually. For example, the processing device 140 may determine a position distance between the focal point and the puncture point and display the focal point and the puncture representation of the at least one puncture parameter when the position difference is less than a threshold. As another example, the processing device 140 may transmit the focal point and the puncture representation of the at least one puncture parameter to the terminal device 130 and display the focal point and the puncture representation of the at least one puncture parameter upon receiving a confirmation from the terminal device 130. As yet another example, the processing device 140 may display the focal point and the puncture representation of the at least one puncture parameter after receiving an instruction from the terminal device 130.

In some embodiments, the processing device 140 may display the focal point and the puncture representation of the at least one puncture parameter in the at least one image of the object or newly captured image(s) of the object.

In some embodiments, the processing device 140 may display the focal point and the puncture representation of the at least one puncture parameter in a 3D model corresponding to the object. As used herein, the 3D model corresponding to the object refers to a 3D model representing various features (e.g., a size, a shape, an appearance, a contour) of the object.

In some embodiments, the 3D model may be pre-established and stored in a storage device (e.g., the storage device 150) disclosed elsewhere in the present disclosure. The processing device 140 may access the storage device 150 and obtain the 3D model. In some embodiments, after obtaining the pre-established 3D model, the processing device 140 may modify or adjust the pre-established 3D according to actual requirements. In some embodiments, the pre-established 3D model may be generated based on statistical data or machine learning. In some embodiments, the 3D model may be established by the processing device 140 based on at least one parameter associated with the object before or during the puncture operation. More descriptions regarding the 3D model corresponding to the object may be found elsewhere in the present disclosure (e.g., FIG. 6 and FIG. 8 and the relevant descriptions thereof).

In some embodiments, the processing device 140 may also determine and/or display a relative position relationship between the focal point and the puncture representation (e.g., a puncture point) of the at least one puncture parameter. In some embodiments, the relative position relationship between the focal point and the puncture point may be represented in various forms. For example, the relative position relationship between the focal point and the puncture point may be represented by a distance (e.g., a vertical distance, a horizontal distance, an actual distance) between the focal point and the puncture point. In some embodiments, the distance may be determined based on a coordinate (e.g., an x-axis coordinate, a y-axis coordinate, a z-axis coordinate) of the focal point and a coordinate (e.g., an x-axis coordinate, a y-axis coordinate, a z-axis coordinate) of the puncture point in a coordinate system (e.g., an image coordinate system or the coordinate system 170). More descriptions regarding the relative position relationship can be found elsewhere in the present disclosure (e.g., FIG. 7 and the descriptions thereof).

In some embodiments, after determining (or displaying) the focal point and the puncture representation of the at least one puncture parameter, the processing device 140 (or a doctor or an operator) may modify or adjust the focal point and/or the at least one puncture parameter according to actual requirements. Further, the processing device 140 may display an adjusted focal point or an adjusted puncture representation (which at least indicates an adjusted puncture point) upon determining that the focal point or at least a portion of the at least one puncture parameter is adjusted.

In some embodiments, after determining (or displaying) the focal point and the puncture representation of the at least one puncture parameter, the processing device 140 may simulate a puncture process based on the focal point and the at least one puncture parameter. The processing device 140 may also display a simulation result of the simulated puncture process in the at least one image (or newly captured image(s)) of the object or the 3D model corresponding to the object. The simulation result may include a simulated puncture point, a simulated end point of the puncture needle, a simulated puncture depth, a simulated puncture angle, a simulated puncture direction, or the like, or a combination thereof.

In some embodiments, the processing device 140 (or a doctor or an operator) may also determine whether the simulation result satisfies a preset condition. For example, the processing device 140 may determine whether a position difference between the simulated end point of the puncture needle and the focal point (or the adjusted focal point) is larger than a difference threshold. In response to determining that the position difference is larger than the difference threshold, the processing device 140 may determine that the simulation result does not satisfy the preset condition; in response to determining that the position difference is less than or equal to the difference threshold, the processing device 140 may determine that the simulation result satisfies the preset condition. As another example, the processing device 140 may determine whether a position difference between the simulated puncture point and the puncture point included in the at least one puncture parameter is larger than a difference threshold. In response to determining that the position difference is larger than the difference threshold, the processing device 140 may determine that the simulation result does not satisfy the preset condition; in response to determining that the position difference is less than or equal to the difference threshold, the processing device 140 may determine that the simulation result satisfies the preset condition.

Further, if the simulation result does not satisfy the preset condition, the processing device 140 (or a doctor or an operator) may adjust the at least one puncture parameter or the focal point based on the simulation result. For example, the processing device 140 may re-determine a puncture needle with another type based on the simulation result. As another example, the processing device 140 may update the puncture depth based on the simulation result. As a further example, the processing device 140 may re-determine an updated puncture point based on the simulated puncture point.

In some embodiments, the simulated puncture process may be repeatedly performed unit the preset condition is satisfied. In some embodiments, the simulated puncture process may be initiated by a user via a simulation button which is set on a control interface of the medical imaging system (e.g., the terminal device 130).

In some embodiments, the processing device 140 may further direct a puncture device (e.g., the puncture device 120) to perform the puncture operation (i.e., an actual puncture operation) on the object based on the (or adjusted) the focal point and the (or adjusted) at least one puncture parameter. In some embodiments, the processing device 140 may update the focal point and/or the puncture representation of the at least one puncture parameter in real time or periodically during the puncture operation. For example, as the puncture needle is inserted into the object, the processing device 140 may update the distance or the spatial relationship between the focal point and the real-time tip point of the puncture needle. Accordingly, the processing device 140 may also display, in the at least one image (or newly captured image(s)) of the object and/or the 3D model corresponding to the object, the focal point and the puncture representation of the at least one puncture parameter during the puncture in real-time or periodically.

According to the embodiments of the present disclosure, the focal point and the puncture representation of the at least one puncture parameter is displayed in the image(s) (e.g., scout image(s)) of the object and/or the 3D model corresponding to the object. Accordingly, according to the focal point and the puncture representation of the at least one puncture parameter, the puncture operation can be accurately and efficiently performed on the object. For example, before the puncture operation (e.g., when the puncture needle preliminarily contacts the object but does not enter the object) or during the puncture operation, the processing device 140 or a user (e.g., a doctor) can modify or adjust the puncture parameter(s) based on the focal point and the puncture representation of at least one puncture parameter. As another example, after the puncture operation, the processing device 140 or a user (e.g., a doctor) can evaluate whether the puncture operation has been successfully executed (e.g., whether a lesion has been removed) based on the focal point and the puncture representation of the at least one puncture parameter.

It should be noted that the above description regarding the process 500 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

Figure 6:
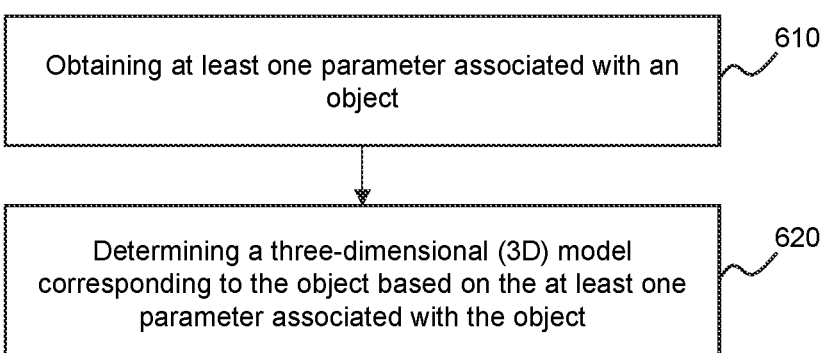
FIG. 6 is a flowchart illustrating an exemplary process for establishing a 3D model corresponding to an object according to some embodiments of the present disclosure.

FIG. 6 is a flowchart illustrating an exemplary process for establishing a 3D model corresponding to an object according to some embodiments of the present disclosure. In some embodiments, process 600 may be an exemplary embodiment of operation 550. In some embodiments, one or more operations of process 600 illustrated in FIG. 6 may be implemented in the medical system 100 illustrated in FIG. 1. For example, the process 600 may be stored in a storage device (e.g., the storage device 150, the storage 220, the storage 390) of the medical system 100 in the form of instructions, and invoked and/or executed by the processing device 140 (e.g., the processor 210, the CPU 340, or one or more modules illustrated in FIG. 4). The operations of the illustrated process presented below are intended to be illustrative. In some embodiments, the process 600 may be accomplished with one or more additional operations not described and/or without one or more of the operations discussed. Additionally, the order in which the operations of the process as illustrated in FIG. 6 and described below is not intended to be limiting.

In 610, the processing device 140 (e.g., the obtaining module 410) may obtain at least one parameter associated with an object.

In some embodiments, the at least one parameter associated with the object may include a size (e.g., a length, a width, a thickness) of the object, a shape of the object, a device parameter of a puncture device (e.g., the puncture device 120), a device parameter of an imaging device (e.g., the imaging device 110), or the like, or a combination thereof. The device parameter of the puncture device may include a puncture range of the puncture device (e.g., a size of the opening of the compression panel 122), a height of the compression panel, a compression pressure of the compression panel, a size of a scanning table (e.g., the scanning table 121), or the like, or a combination thereof. The device parameter of the imaging device may include a rotation diameter of a radioactive scanning source (e.g., the radioactive scanning source 112), a rotation angle of the radioactive scanning source, a position of the radioactive scanning source, or the like, or any combination thereof.

In some embodiments, the processing device 140 may obtain the at least one parameter associated with the object from one or more components of the medical system 100. For example, the at least one parameter associated with the object may be stored in a storage device (e.g., the storage device 150, the storage 220, or the storage 390) of the medical system 100. The processing device 140 may access the storage device and obtain the at least one parameter associated with the object. As another example, the processing device 140 may obtain the at least one parameter associated with the object based on a scanning protocol of the object.

In 620, the processing device 140 (e.g., the display module 440) may determine a 3D model corresponding to the object based on the at least one parameter associated with the object.

In some embodiments, the processing device 140 may determine at least one model parameter based on the at least one parameter associated with the object and determine the 3D model based on the at least one model parameter. The at least one model parameter may include a shape, a size (e.g., a length, a width, a thickness), or the like, or a combination thereof, of the 3D model.

In some embodiments, the size of the 3D model may be the same or different from that of the object. For example, the processing device 140 may designate a compressed (e.g., compressed by the compression panel 122) thickness of the object as the thickness of the 3D model. As another example, the processing device 140 may designate the length and the width (e.g., a length and a width of an opening) of the compression panel as the length and the width of the 3D model, respectively.

In some embodiments, the shape of the 3D model may be various, for example, a cuboid, a cube, a cylinder, a cone, a pyramid, a prism, a sphere, a hemisphere, or an irregular shape. In some embodiments, the shape of the 3D model may be determined based on the shape of the object. For example, it is assumed that the object is the breast of a patient, the shape of the 3D model may be a semi-hemisphere. As another example, it is assumed that the object is the head of the patient, the shape of the 3D model may be a sphere.

In some embodiments, the processing device 140 may determine the 3D model based on a modeling algorithm. Exemplary modeling algorithm may include a Triangular/Tetrahedral (Tri/Tet) technique (e.g., an Octree algorithm, an Advancing Front algorithm, a Delaunay algorithm, etc.), a Quadrilateral/Hexahedra (Quad/Hex) technique (e.g., a Trans-finite Interpolation (TFI) algorithm, an Elliptic algorithm, etc.), a hybrid technique, a parametric model-based technique, a surface meshing technique, or the like, or any combination thereof.

In some embodiments, the processing device 140 may obtain a preliminary 3D model from a model library and determine the 3D model corresponding to the object by adjusting the parameter(s) of the preliminary 3D model.

It should be noted that the above description regarding the process 600 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

Figure 7:
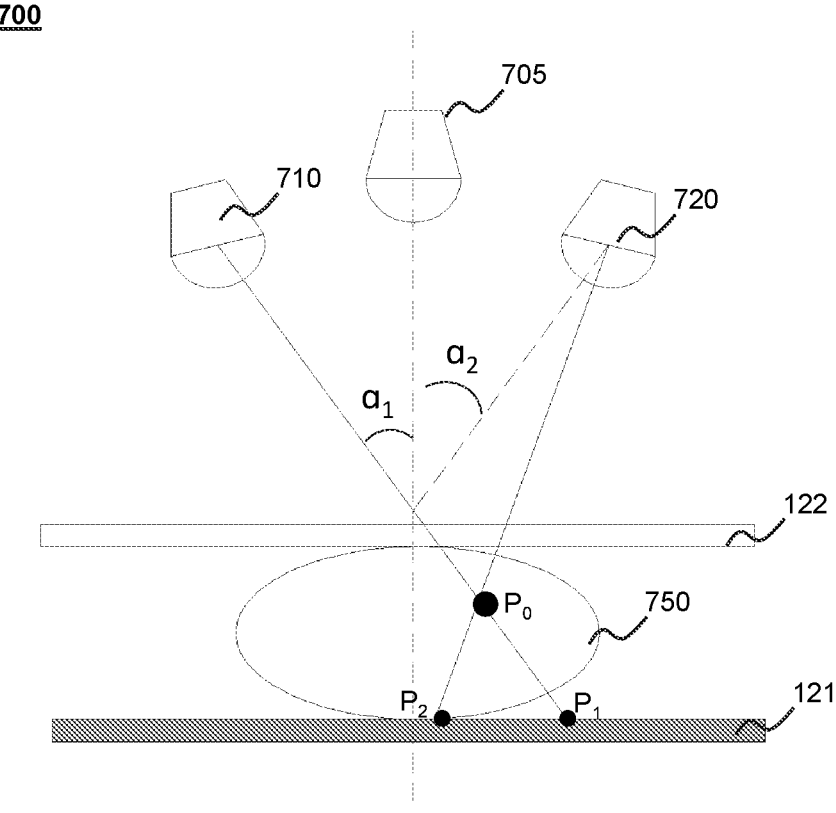
FIG. 7 is a schematic diagram illustrating an exemplary coordinate relationship between a focal point and at least one image including the focal point according to some embodiments of the present disclosure.

FIG. 7 is a schematic diagram illustrating an exemplary coordinate relationship between a focal point and at least one image including the focal point according to some embodiments of the present disclosure.

As illustrated in FIG. 7, an imaging device includes a radioactive scanning source which is generally located at a $0°$ position 705 and can rotate within a rotation range (e.g., from position 710 to position 720). The radioactive scanning source may emit radioactive rays to an object 750 and accordingly image(s) of the object 750 can be captured. For example, a first image corresponding to position 710 (which corresponds to an angle $\alpha_1$) and a second image corresponding to position 720 (which corresponds to an angle $\alpha_2$) may be captured.

Further, as described in connection with operation 520 and operation 530, the processing device 140 may determine a focal point $P_1$ representing a physical point $P_0$ of the object 750 in the first image and determine a focal point $P_2$ representing the physical point $P_0$ in the second image. The processing device 140 may also determine a relative position relationship between the focal point (e.g., the focal point $P_1$, the focal point $P_2$, or the physical point (i.e., $P_0$)) and a puncture point included in the at least one puncture parameter.

As illustrated in FIG. 7, in the coordinate system 170, a coordinate of the focal point $P_1$ may be represented by ($x_{p1}$, $y_{p1}$, $z_{p1}$), and a coordinate of the radioactive scanning source at position 710 may be represented by ($x_b$, $y_b$, $z_b$). Accordingly, the coordinate of the focal point $P_1$ and the coordinate of the radioactive scanning source at position 710 satisfy Equation (1) below:

$$\frac{x - x_b}{x_{p1} - x_b} = \frac{y - y_b}{y_{p1} - y_b} = \frac{z - z_b}{z_{p1} - z_b} \tag{1}$$

where (x, y, z) refers to any point on a first line connecting the focal point $P_1$ and the radioactive scanning source at position 710.

Similarly, a coordinate of the focal point $P_2$ may be represented by ($x_{p2}$, $y_{p2}$, $z_{p2}$) and a coordinate of the radioactive scanning source at position 720 may be represented by ($x_c$, $y_c$, $z_c$). Accordingly, the coordinate of the focal point $P_2$ and the coordinate of the radioactive scanning source at position 720 satisfy Equation (2) below:

$$\frac{x - x_c}{x_{p2} - x_c} = \frac{y - y_c}{y_{p2} - y_c} = \frac{z - z_c}{z_{p2} - z_c} \tag{2}$$

where (x, y, z) refers to any point on a second line connecting the focal point $P_2$ and the radioactive scanning source at position 710.

In some embodiments, the coordinate (i.e., ($x_b$, $y_b$, $z_b$)) of the radioactive scanning source at position 710 and the coordinate (i.e., ($x_c$, $y_c$, $z_c$)) of the radioactive scanning source at position 720 may be determined based on the at least one parameter associated with the object. For example, the coordinate of the radioactive scanning source at position 710 and the coordinate of the radioactive scanning source at position 720 may be determined according to Equation (3) and Equation (4) below, respectively:

$$(x_b, y_b, z_b) = \left(\frac{1}{2}L_{FPD} - L_R\sin\alpha_1, W_{FPD}, H - (L_R - L_R\cos\alpha_1)\right) \quad (3)$$

$$(x_c, y_c, z_c) = \left(\frac{1}{2}L_{FPD} + L_R\sin\alpha_2, W_{FPD}, H - (L_R - L_R\cos\alpha_2)\right) \quad (4)$$

where $L_R$ represents a rotation diameter of the radioactive scanning source, $W_{FPD}$ represents a width of the scanning table, and $L_{FPD}$ represents a length of the scanning table.

Further, it can be seen from FIG. 7 that the first line and the second line interest at the physical point $P_0$. Accordingly, according to the above Equations, a coordinate of the physical point $P_0$ (i.e., the actual focal point) can be determined. Furthermore, the relative position relationship between the focal point and the puncture point under the coordinate system 170 can be determined.

Figure 8:
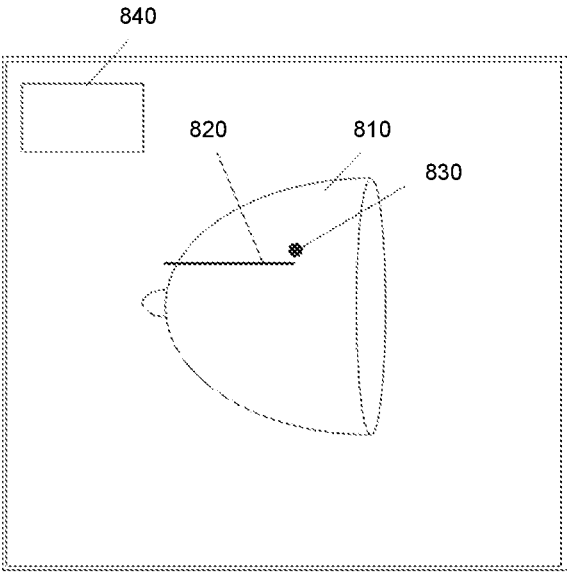
FIG. 8 is a schematic diagram illustrating an exemplary display of a focal point and a puncture representation of at least one puncture parameter according to some embodiments of the present disclosure.

FIG. 8 is a schematic diagram illustrating an exemplary display of a focal point and a puncture representation of at least one puncture parameter according to some embodiments of the present disclosure. As illustrated in FIG. 8, 810 refers to a 3D model corresponding to a breast of a patient, 820 refers to a puncture representation (which indicates a puncture needle and a puncture point (a tip point of the puncture needle can be understood as the puncture point)), and 830 refers to a focal point. It can be seen that before, during, or after the puncture operation, the focal point 830 and the puncture representation 820 may be displayed in the 3D model, which can provide a reference for a user (e.g., a doctor). Further, a notification area 840 including notification information also may be displayed. For example, the notification information may include a position difference between the focal point 830 and the tip point of the puncture needle, a position difference between a papilla of the breast and a tip point of the puncture needle, etc.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure, or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures, or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A non-transitory computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object-oriented programming language such as Java, Scala, Smalltalk, Eiffel, JADE, Emerald, C++, C #, VB. NET, Python or the like, conventional procedural programming languages, such as the "C" programming language, Visual Basic, Fortran 2003, Perl, COBOL 2002, PHP, ABAP, dynamic programming languages such as Python, Ruby, and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed object matter requires more features than are expressly recited in each claim. Rather, inventive embodiments lie in less than all features of a single foregoing disclosed embodiment.

In some embodiments, the numbers expressing quantities, properties, and so forth, used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting effect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A method implemented on a computing device having at least one processor and at least one storage device, the method comprising:

causing an imaging device to scan an object to capture at least one image of the object that includes at least one scout image of the object;

determining a focal point in each of the at least one scout image;

automatically determining at least one puncture parameter of a puncture operation to be performed on the object based on information associated with the focal point;

displaying, during the puncture operation, the focal point and a puncture representation of the at least one puncture parameter in a three-dimensional (3D) model of the object, the puncture representation at least indicating a puncture needle within the object and a puncture point that is a tip point of the puncture needle, a position difference between a papilla of the object and the tip point of the puncture needle being displayed in the 3D model;

updating the puncture representation during the puncture operation in real-time; and displaying the puncture representation during the puncture operation in real-time.

2. The method of claim 1, the displaying the focal point and the puncture representation of the at least one puncture parameter comprising:

displaying the focal point and the puncture representation of the at least one puncture parameter in the at least one image of the object.

3. The method of claim 1, wherein the 3D model corresponding to the object is established based on a process including:

obtaining at least one object parameter associated with the object, the object parameter associated with the object including at least one of a size of the object or a device parameter of a puncture device; and determining the 3D model corresponding to the object based on the at least one object parameter associated with the object.

4. The method of claim 1, wherein the at least one puncture parameter includes at least one of a position of the puncture point, a type of the puncture needle, a length of the puncture needle, a diameter of the puncture needle, a puncture direction, a puncture angle, or a puncture depth.

5. The method of claim 1, further comprising:

simulating a puncture process based on the focal point and the at least one puncture parameter associated with the puncture operation to be performed on the object; and displaying a simulation result of the simulated puncture process in at least one of the at least one image of the object and/or a 3D model corresponding to the object.

6. The method of claim 5, further comprising:

determining whether the simulation result satisfies a preset condition, wherein the preset condition includes a position difference between a simulated end point of a puncture needle, and the focal point or an adjusted focal point is less than or equal to a difference threshold, and/or a position difference between a simulated puncture point and the puncture point included in the at least one puncture parameter is less than or equal to the difference threshold; and in response to determining that the simulation result does not satisfy the preset condition, adjusting the focal point or the at least one puncture parameter based on the simulation result, and directing a puncture device to perform the puncture operation on the object based on the adjusted focal point and at least one adjusted puncture parameter.

7. The method of claim 1, further comprising:

displaying an adjusted focal point or an adjusted puncture representation upon determining that the focal point or at least a portion of the at least one puncture parameter is adjusted, the adjusted puncture representation at least indicating an adjusted puncture point.

8. The method of claim 1, further comprising:

upon determining that the focal point or at least a portion of the at least one puncture parameter is adjusted, directing a puncture device to perform the puncture operation on the object based on an adjusted focal point or an adjusted at least one puncture parameter.

9. The method of claim 1, further comprising:

evaluating, by the processing device, whether the puncture operation has been successfully executed based on the focal point and the puncture representation of the at least one puncture parameter after the puncture operation.

10. The method of claim 1, wherein a position difference between the focal point and the tip point of the puncture needle within the object is displayed in the 3D model.

11. The method of claim 10, further comprising:

obtaining a first image captured by scanning the object using the imaging device at a first angle, and a second image captured by scanning the object using the imaging device at a second angle;

determining a first three-dimensional (3D) coordinate of a radioactive scanning source of the imaging device at the first angle based on a rotation diameter of the radioactive scanning source, a width of a scanning table, a length of the scanning table, and the first angle;

determining a second 3D coordinate of the radioactive scanning source at the second angle based on the rotation diameter of the radioactive scanning source, the width of the scanning table, the length of the scanning table, and the second angle;

determining a first 3D coordinate of a first focal point representing a physical point of the object in the first image based on the first 3D coordinate of the radioactive scanning source;

determining a second 3D coordinate of a second focal point representing the physical point of the object in the second image based on the second 3D coordinate of the radioactive scanning source;

determining a coordinate of the physical point based on the first 3D coordinate and the second 3D coordinate of the radioactive scanning source, the first 3D coordinate of the first focal point, and the second 3D coordinate of the second focal point; and determining a relative position relationship between the puncture point and at least one of the first focal point, the second focal point, or the physical point based on the coordinate of the physical point, the first 3D coordinate of the first focal point, and the second 3D coordinate of the second focal point.

12. The method of claim 1, wherein a notification area including notification information is displayed synchronously with the focal point, the puncture representation, and the 3D model; and the notification information includes a position difference between the focal point and the tip point of the puncture needle and/or the position difference between the papilla of the object and the tip point of the puncture needle.

13. The method of claim 1, wherein the focal point and the puncture representation of the at least one puncture parameter is displayed in the at least one scout image and the 3D model; and when the focal point or the at least one puncture parameter is modified or adjusted in the at least one scout image, an adjusted focal point or an adjusted puncture representation is displayed in the 3D model upon determining that the focal point or the at least one puncture parameter is adjusted.

14. A system, comprising:

at least one storage device including a set of instructions; and at least one processor configured to communicate with the at least one storage device, wherein when executing the set of instructions, the at least one processor is configured to direct the system to perform operations including:

causing an imaging device to scan an object to capture at least one image of the object that includes at least one scout image of the object;

determining a focal point in each of the at least one scout image;

automatically determining at least one puncture parameter of a puncture operation to be performed on the object based on information associated with the focal point;

displaying, during the puncture operation, the focal point and a puncture representation of the at least one puncture parameter in a three-dimensional (3D) model of the object, the puncture representation at least indicating a puncture needle within the object and a puncture point that is a tip point of the puncture needle, a position difference between a papilla of the object and the tip point of the puncture needle being displayed in the 3D model;

updating the puncture representation during the puncture operation in real-time; and displaying the puncture representation during the puncture operation in real-time.

15. The system of claim 14, wherein the 3D model corresponding to the object is established based on a process including:

obtaining at least one object parameter associated with the object, the object parameter associated with the object including at least one of a size of the object or a device parameter of a puncture device; and determining the 3D model corresponding to the object based on the at least one object parameter associated with the object.

16. The system of claim 14, wherein the at least one puncture parameter includes at least one of a position of the puncture point, a type of the puncture needle, a length of the puncture needle, a diameter of the puncture needle, a puncture direction, a puncture angle, or a puncture depth.

17. The system of claim 14, further comprising:

simulating a puncture process based on the focal point and the at least one puncture parameter associated with the puncture operation to be performed on the object; and displaying a simulation result of the simulated puncture process in at least one of the at least one image of the object and/or a 3D model corresponding to the object.

18. The system of claim 17, further comprising:

determining whether the simulation result satisfies a preset condition, wherein the preset condition includes a position difference between a simulated end point of a puncture needle, and the focal point or an adjusted focal point is less than or equal to a difference threshold, and/or a position difference between a simulated puncture point and the puncture point included in the at least one puncture parameter is less than or equal to the difference threshold; and in response to determining that the simulation result does not satisfy the preset condition, adjusting the focal point or the at least one puncture parameter based on the simulation result, and directing a puncture device to perform the puncture operation on the object based on the adjusted focal point and at least one adjusted puncture parameter.

19. The system of claim 14, further comprising:

displaying an adjusted focal point or an adjusted puncture representation upon determining that the focal point or at least a portion of the at least one puncture parameter is adjusted, the adjusted puncture representation at least indicating an adjusted puncture point.

20. A non-transitory computer readable medium, comprising a set of instructions, wherein when executed by at least one processor, the set of instructions direct the at least one processor to effectuate a method, the method comprising:

causing an imaging device to scan an object to capture at least one image of the object that includes at least one scout image of the object;

determining a focal point in each of the at least one scout image;

automatically determining at least one puncture parameter of a puncture operation to be performed on the object based on information associated with the focal point;

displaying, during the puncture operation, the focal point and a puncture representation of the at least one puncture parameter in a three-dimensional (3D) model of the object, the puncture representation at least indicating a puncture needle within the object and a puncture point that is a tip point of the puncture needle, a position difference between a papilla of the object and the tip point of the puncture needle being displayed in the 3D model;

updating the puncture representation during the puncture operation in real-time; and displaying the puncture representation during the puncture operation in real-time.

* * * * *